United States Patent
Yuan (10) Patent No.: US 8,934,708 B2
(45) Date of Patent: *Jan. 13, 2015

(54) VOLUMETRIC IMAGE DATA PROCESSING

(71) Applicant: Peking University, Beijing (CN)

(72) Inventor: Xiaoru Yuan, Beijing (CN)

(73) Assignee: Peking University, Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 13/837,956

(22) Filed: Mar. 15, 2013

(65) Prior Publication Data

US 2013/0279798 A1 Oct. 24, 2013

Related U.S. Application Data (63) Continuation of application No. 12/569,480, filed on Sep. 29, 2009, now Pat. No. 8,437,538.

(51) Int. Cl.
 G06K 9/00 (2006.01)
 G06T 15/00 (2011.01)
 G06T 17/00 (2006.01)
 A61B 5/0476 (2006.01)

(52) U.S. Cl.
 CPC ............... *G06T 15/005* (2013.01); *G06T 17/00* (2013.01); *A61B 5/0476* (2013.01)
 USPC ........................................................ 382/154

(58) Field of Classification Search
 None
 See application file for complete search history.

(56) References Cited

U.S. PATENT DOCUMENTS

| 2005/0174347 A1 | 8/2005 | Visser |
| 2008/0161636 A1 | 7/2008 | Hurme et al. |
| 2008/0267479 A1 | 10/2008 | Jago |
| 2010/0278405 A1 | 11/2010 | Kakadiaris et al. |

FOREIGN PATENT DOCUMENTS

| CN | 1650329 | 8/2005 |
| CN | 101331406 | 12/2008 |
| CN | 101517618 | 8/2009 |
| JP | 10118061 | 5/1998 |
| JP | 10320544 | 12/1998 |
| WO | 2007/069174 | 6/2007 |

OTHER PUBLICATIONS

Suenaga Yasuhito, et al, "Image Processing Technologies for Emerging Medical Services" Aug. 1, 2007, 90th, vol. 8, p. 642-650.

(Continued)

*Primary Examiner* — Vikkram Bali
(74) *Attorney, Agent, or Firm* — Brundidge & Stanger, P.C.

(57) ABSTRACT

A method, apparatus, computer readable medium storing computer readable instructions are disclosed for processing volumetric image data. According to the method, 3-dimensional data points are collected. A plurality of 2-dimensional image maps is obtained from the 3-dimensional data points. At least one of the plurality of 2D image maps is extracted to form at least one image frame. A frame gallery is created from the at least one image frame.

21 Claims, 9 Drawing Sheets

(56) References Cited

OTHER PUBLICATIONS

Drebin, R. A, et al., "Volume Rendering," Computer Graphics, vol. 22, Issue: 4, pp. 65-74, Aug. 1988.

Fabiani, M., et al., "Event-Related Brain Potentials: Methods, Theory, and Applications," Handbook of Psychophysiology, 3rd. edition, Cambridge University Press, 2007, pp: 85-119.

Molinari., et al., "Comparison of algorithms for non-linear inverse 3D electrical tomography reconstruction," Physiological Measurement, 2002, vol. 23, pp: 95-104.

International Search Report and Written Opinion for International Application No. PCT/CN2010/073001 mailed on Sep. 2, 2010.

Fast Remote Isosurface Visualization with Chessboarding, by Neeman et al., The eurographics association 2004.

Briggs et al., "A Real-Time Volumetric Visualization System for Electrical Impedance Tomography", Physiol. Meas. vol. 21, 2000, pp. 27-33.

Daniel et al., "Video Visualization", Proceedings of the 14th IEEE Visualization Conference, 2003, pp. 409-416.

Hege et al., "Visualizing Time-Varying ERP Data", IEEE-VGTC Symposium on Visualization, vol. 28, No. 3, 2009, pp. 1-8.

Jung et al., "Analysis and Visualization of Single-Trial Event-Related Potentials", Human Brain Mapping, vol. 14, 2001, pp. 166-185.

Tyler S. Lorig, "Spatio-Temporal Display of Event-Related Potential Data in Three Dimensions", Brain Topography, vol. 8, No. 1, 1995, pp. 3-6.

Yuan et al., "HDR VolVis: High Dynamic Range Volume Visualization", IEEE Transactions on Visualization and Computer Graphics, vol. 12, No. 4, Jul./Aug. 2006, pp. 433-445.

VOLUMETRIC IMAGE DATA PROCESSING

BACKGROUND 3-dimensional ("3D") data sets may be generated from measuring points spanning in a 3D space such as spherical surface. The data sets are processed to provide useful information related to the 3-dimensional space. For example, the time-varying Event-Related Potential ("ERP") data in cognitive neuroscience is measured from electrodes positioned on different locations at the scalp of a person. The ERP data collected allows scientist to observe human brain activity that reflects specific cognitive processes at a specific time. A comprehensive understanding of the complex temporal-spatial correlation of time-varying ERP, particularly when there are many data sets from 3D space generated over time, relies upon how the data sets are functionally interpreted and processed for visualization.

SUMMARY

One embodiment of the present disclosure describes a method for processing volumetric image data. This method includes obtaining a plurality of 2-dimensional image maps from 3-dimensional data points, extracting at least one of the plurality of 2-dimensional image maps to form at least one image frame, and creating a frame gallery from the at least one image frame.

Further, the aforementioned method, or any part thereof, may be performed by a computing device under the direction of a computer program embodied on a computer readable medium.

Further, the aforementioned method, or any part thereof, may be performed to obtain a composite image data.

An alternative embodiment of the present disclosure describes an apparatus for processing volumetric image data comprising an obtaining unit that obtains a plurality of 2-dimensional image maps from 3-dimensional data points; an extracting unit that extracts at least one of the plurality of 2-dimensional image maps to form at least one image frame; and a creating unit that creates a frame gallery from the at least one image frame.

Another alternative embodiment of the present disclosure describes a method for processing volumetric image data. This method includes steps of obtaining a plurality of 2-dimensional image maps from 3-dimensional data points, extracting at least one of the plurality of 2-dimensional image maps to form at least one image frame, and determining at least one of a radically different frame and a representative frame.

Further, the aforementioned method, or any part thereof, may be performed by a computing device under the direction of a computer program embodied on a computer readable medium.

Another alternative embodiment of the present disclosure describes an apparatus for processing volumetric image data comprising an obtaining unit that obtains a plurality of 2-dimensional image maps from 3-dimensional data points; an extracting unit that extracts at least one of the plurality of 2-dimensional image maps to form at least one image frame; and a determining unit that determines at least one of a radically different frame and a representative frame.

Another alternative embodiment of the present disclosure describes a method for processing volumetric image data. The method includes the steps of obtaining a plurality of 2-dimensional image maps from 3-dimensional data points, constructing a volumetric image data based on the plurality of 2-dimensional image maps and temporal data associated with each of the plurality of 2-dimensional image maps and applying a critical point graph to the volumetric image data.

Further, the aforementioned method, or any part thereof, may be performed by a computing device under the direction of a computer program embodied on a computer readable medium.

Further, the aforementioned method, or any part thereof, may be performed to obtain a composite image data.

Another alternative embodiment of the present disclosure describes an apparatus for processing volumetric image data comprising an obtaining unit that obtains a plurality of 2-dimensional image maps from 3-dimensional data points; a constructing unit that constructs a volumetric image data based on the plurality of 2-dimensional image maps and temporal data associated with each of the plurality of 2-dimensional image maps; and an applying unit that applies a critical point graph to the volumetric image data.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWING

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Introduction

This disclosure is drawn, inter alia, to methods, apparatuses and computer readable mediums storing computer programs related to processing volumetric image data for visualization. Specifically, the present disclosure describes a framework for visualization of data sets from spherical surface such as ERP data. This disclosure describes that a volumetric image data may be constructed from 2D image maps that are obtained from 3D data sets. Critical image frames are formed by extracting 2D image maps from the volumetric image data. A frame gallery may be created based on the image frames. Image data and composite image data are produced from the volumetric image data and the frame gallery for rendering.

The visualization of the volumetric image data may be implemented to further include analysis of a critical point graph and iso-surfaces of the volumetric image data. Thus, a comprehensive understanding of a complex temporal-spatial correlation of time-varying data sets may be provided by examining the frame gallery, critical point graph, iso-surfaces and the volumetric image data with interactive rendering and visualization features. In addition, when only critical image frames are transmitted, a bandwidth required to communicate data for visualization of a volumetric image data in a network is significantly less when compared to a case of transmitting the entire volumetric image data.

Overview of the Network Environment

Figure 1:
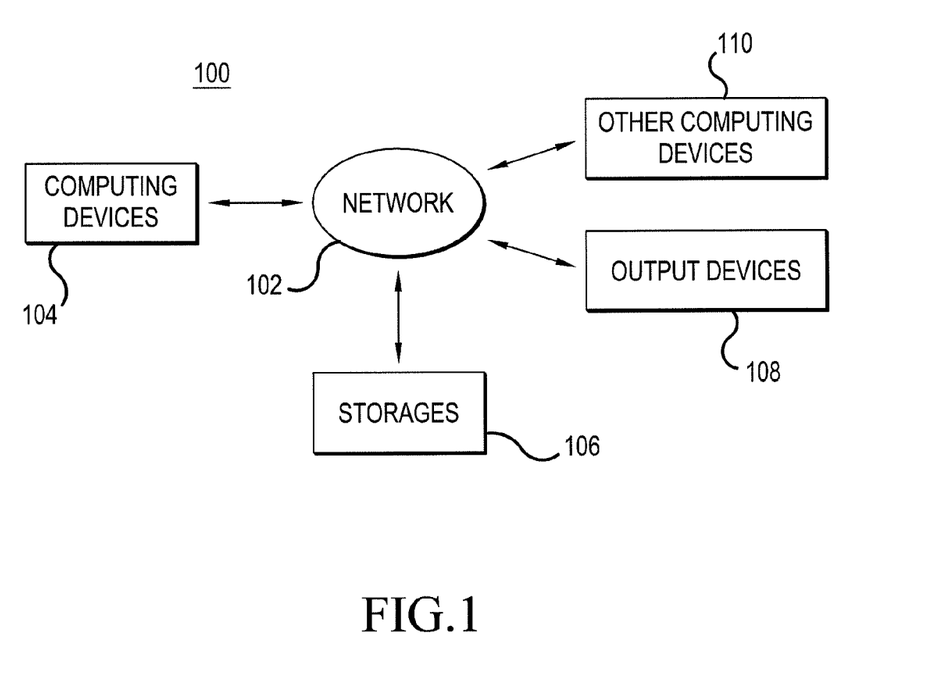
FIG. 1 is a block diagram illustrating an example network environment.
Figure 2:
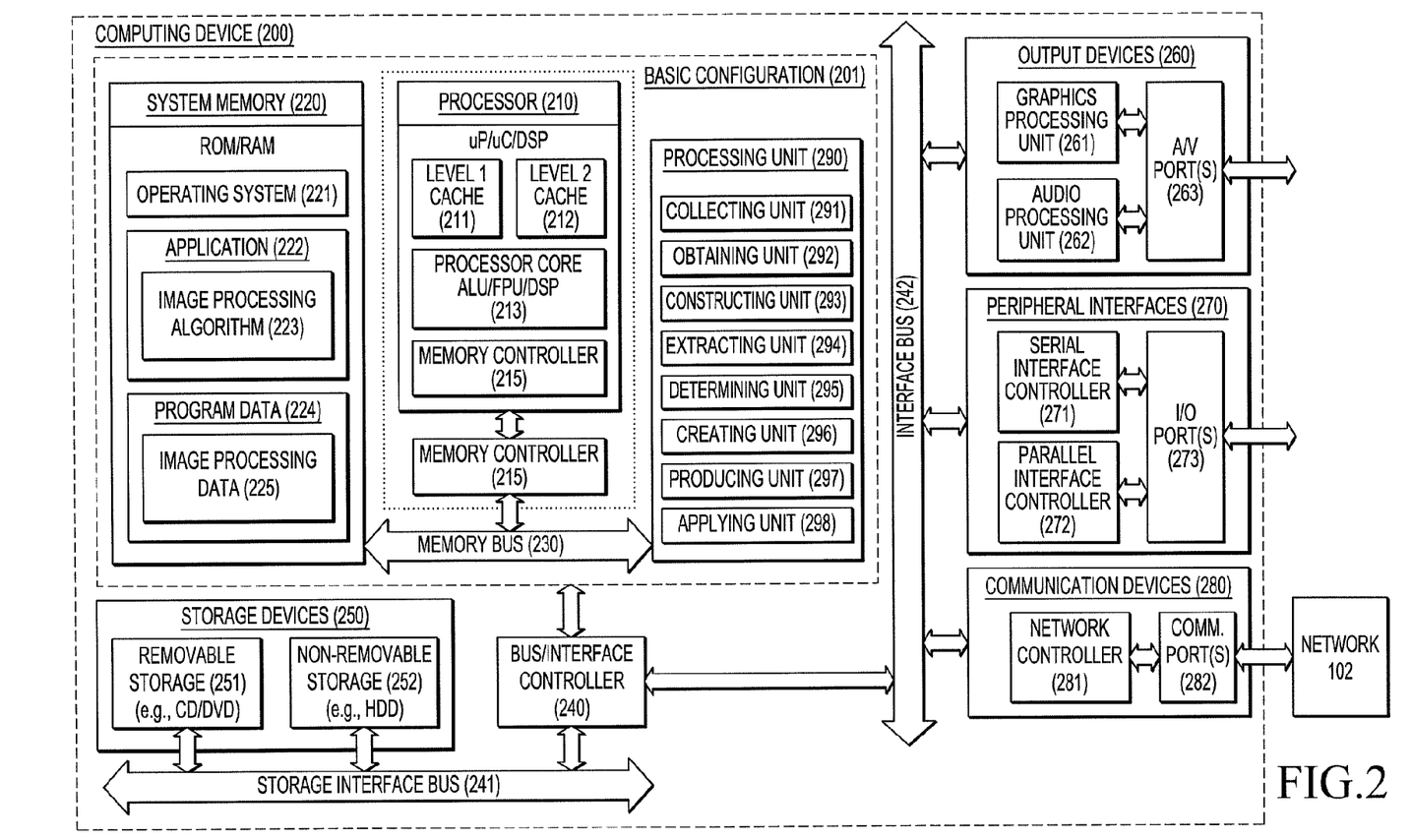
FIG. 2 is a block diagram illustrating an example computing device arranged to process volumetric image data according to some embodiments of the present disclosure.

FIG. 1 is a block diagram illustrating a network environment 100 in which the methods, computer programs, and apparatus relating to process volumetric image data may be implemented. The network environment 100 contains a network 102, which provides communication links between various devices thereby connecting the devices together within the network environment. Network 100 may be implemented as, for example a wide area network, a local area network, etc., and may include connections that are wired, or wireless connections. FIG. 1 also shows computing devices 104 connected to network 102. In addition, storages 106, output devices 108 and other computing devices 110 may also be connected to the network 102. The network environment 100 may include additional devices connected to the network 102 not shown. An example of a computing device 104, 110 is illustrated in FIG. 2 as computing device 200. It may be appreciated that, alternatively, the system environment may include a computing device that includes all of the components at the computing device wherein a network connection is not required.

Example of Apparatus Implementation

FIG. 2 is a block diagram illustrating an example computing device 200 that may be arranged for volumetric image data processing in accordance with the present disclosure. In a very basic configuration 201, computing device 200 typically includes one or more processors 210 and system memory 220. A memory bus 230 can be used for communicating between the processor 210, the system memory 220, and the processing units 290.

Depending on the desired configuration, processor 210 can be of any type including but not limited to a microprocessor ($\mu$P), a microcontroller ($\mu$C), a digital signal processor (DSP), or any combination thereof. Processor 210 can include one more levels of caching, such as a level one cache 211 and a level two cache 212, a processor core 213, and registers 214. The processor core 213 can include an arithmetic logic unit (ALU), a floating point unit (FPU), a digital signal processing core (DSP Core), or any combination thereof. A memory controller 215 can also be used with the processor 210, or in some implementations the memory controller 215 can be an internal part of the processor 210.

Depending on the desired configuration, the system memory 220 can be of any type including but not limited to volatile memory (such as RAM), non-volatile memory (such as ROM, flash memory, etc.) or any combination thereof. System memory 220 typically includes an operating system 221, one or more applications 222, and program data 224. Applications 222 includes image processing algorithm 223 that may be arranged to process 3D data points to generate volumetric image data. Program Data 224 includes image processing data 225 that may be used for process volumetric image data, as will be further described below. In some embodiments, application 222 can be arranged to operate with program data 224 on an operating system 221 such that volumetric image data may be generated. This described basic configuration is illustrated in FIG. 2 by those components within dashed line 201.

Depending on the desired configuration, the processing units 290 may include a collecting unit 291 that collects 3-D data points, an obtaining unit 292 that obtains a plurality of 2-D image maps from 3-D data points, a constructing unit 293 that constructs a volumetric image data based on the plurality of 2-dimensional image maps and temporal data associated with each of the plurality of 2-dimensional image maps, an extracting unit 294 that extracts at least one of the plurality of 2-dimensional image maps to form at least one image frame, a determining unit 295 that determines at least one of a radically different frame and a representative frame, a creating unit 296 that creates a frame gallery from the at least one image frame, a producing unit 297 that produces an image data or a composite image data, and an applying unit 298 that applies a critical point graph to the volumetric data.

Computing device 200 can have additional features or functionality, and additional interfaces to facilitate communications between the basic configuration 201 and any required devices and interfaces. For example, a bus/interface controller 240 can be used to facilitate communications between the basic configuration 201 and one or more data storage devices 250 via a storage interface bus 241. The data storage devices 250 can be removable storage devices 251, non-removable storage devices 252, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 220, removable storage 251 and non-removable storage 252 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 200. Any such computer storage media can be part of device 200.

Computing device 200 can also include an interface bus 242 for facilitating communication from various interface devices (e.g., output interfaces, peripheral interfaces, and communication interfaces) to the basic configuration 201 via the bus/interface controller 240. Example output devices 260 include a graphics processing unit 261 and an audio processing unit 262, which can be configured to communicate to various external devices such as a display or speakers via one or more A/V ports 263. Example peripheral interfaces 270 include a serial interface controller 271 or a parallel interface controller 272, which can be configured to communicate with external devices such as input devices (e.g., keyboard, mouse, pen, voice input device, touch input device, etc.) or other peripheral devices (e.g., printer, scanner, etc.) via one or more I/O ports 273. An example communication device 280 includes a network controller 281, which can be arranged to facilitate communications with the network 102 in FIG. 1 via one or more communication ports 282. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media. The term computer readable media as used herein can include both storage media and communication media.

Computing device 200 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 200 can also be implemented as a personal computer including both laptop computer and non-laptop computer configurations.

Example of Flow Process Implementation—Frame Gallery

Figure 3:
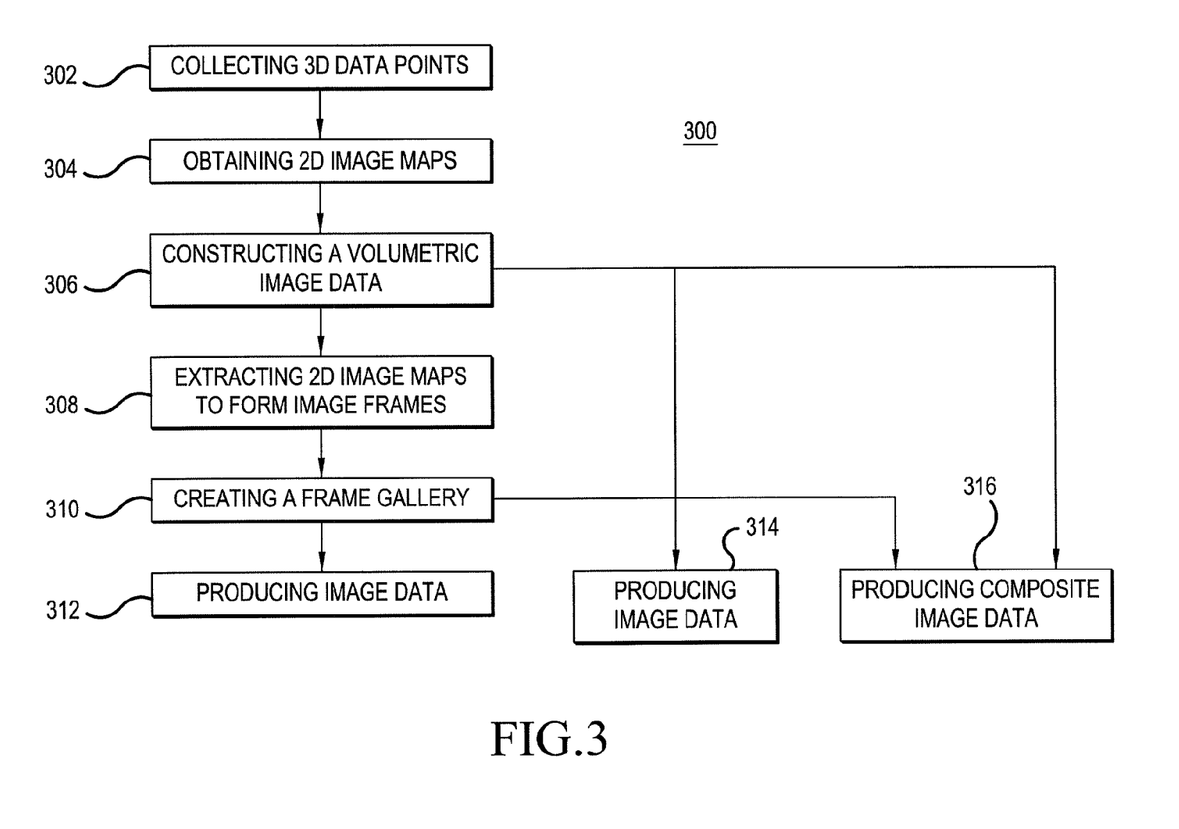
FIG. 3 is a flow diagram illustrating an example volumetric image data processing method according to some embodiments of the present disclosure.

FIG. 3 is a flow diagram depicting a volumetric image data process in accordance with one embodiment. Referring to the process flow 300, in step 302, data sets of 3D data points are collected to obtain 2-dimensional ("2D") image maps in step 304. In step 302, the 3D data points 302 may be collected from measurements carried out with measuring points spanning in 3D space. 3D data sets are generated from a spherical surface such as the event-related potential (ERP) data, ground measurement data, atmosphere temperature data and the like. For the purpose of discussion, ERP data sets generated over time will be used as a specific example. However, it should be understood that the methods, computer program and apparatus described herein may be applied to other data sets from the spherical surface. ERP data may be considered as a four-dimensional data set consisting of three spatial dimensions and time. ERP data is a group of potentials measured at different sensors over scalp of a person.

In step 304, the position of the measurement points of an ERP data of a specific time may be mapped to a 2D plane by projecting the original points in 3D space to a 2D plane by using a surface parameterization method. The surface parameterization method capable of minimizing distortion or minimizing computing effort may be chosen advantageously. A rectangle on the 2D plane may be defined as one that can just cover all the projected points. Other shapes capable of covering all the projected points may be employed as well. The rectangle has certain resolution, which may be defined by acquiring an input from, for example, a user, to form a 2D image map. The image map may be a black-white one. A typical resolution could be N×N or M×N, e.g. 512×512, 512× 256 and 256×256 as some examples. Each of the projected points has a position, i.e. coordinate, on the 2D image map. Data values of pixels not plotted in the 2D image map may be interpolated based on the neighboring pixels with the values assigned. One option could be a process where all plotted points are triangulated by using Delaunay Triangulation first, and then interpolation may be carried out at the 2D image map by using Barycentric interpolation. The whole process may be carried out by using OpenGL APIs provided at chip level so as to save processing time. The ERP potentials may be plotted as intensity/gray scale at different points on the 2D image map, where all potential values experience a scaling process so as to fall into a gray scale range from 0% to 100%.

Steps 302 and 304 are performed on the ERP data taken from different times. In step 306, a volumetric image data is constructed from the 2D image maps generated in step 304. With each ERP volume slice, i.e., each image generated, an ERP volume may be constructed by stacking all data slices together along the time dimension. The ERP volume data includes the information of the ERP data of the whole time range. Because of the high temporal resolution of the ERP technique, ERP data sets usually contain thousands of sampling time points. Truncation on the data set and evenly sampling data at the time coordinate may be performed to reduce the size of the data set. 3D Gaussian filtering may also be performed on the data volume to reduce noise.

The ERP paradigm may further involve at least two experimental conditions and an ERP volume may be generated for each of the experimental conditions. A difference volume may be generated by calculating the difference between the ERP volumes of the different experimental conditions. Furthermore, in constructing the volumetric image data, an iso-surface extraction process may be applied to generate an iso-surface at certain value. Iso-surface extraction could be performed on both volumes generated from a single ERP data set and difference volumes. The classic marching cubes algorithm may be implemented.

Further, critical point graphics (CPG) may also be applied to the volumetric image data. The gradient field of the original data volume may be computed. Critical points are computed based the eigenvalues and eigenvectors of the Jacobian matrix. The critical point graph (CPG) may be generated with the computed critical points and streamlines in between. The streamlines are tangent to the vector field direction defined in each given point. In the case of ERP, the structure of the computed CPG may be an indication of the underlying brain activity.

In one embodiment, the process flow may proceed to step 314 to produce an image data based on the volumetric image data obtained in step 306. The image data may be rendered by a volume rendering method applicable such as volume ray casting, splatting, shear wrap, texture mapping and the like. A volume rendering method may be selected considering processing speed and computing complexity. When performing volume rendering, a transfer function may be employed. For example, the transfer function could be a look-up table mapping the value of pixels into color or transparency. In the transfer function, the values close to zero may be represented by, for example, green which may be a "neutral" color in most people's perception. The positive values may be represented by "warm" colors such as yellow and red and the negative values are represented by "cool" colors such as blue and cyan. The transfer function may also be designed so that the large quantity of data close to zero are made more transparent while the data close to the two extremes are assigned higher opacity. The transfer function may be defined and inputted by a user. The rendering of the volumetric image data may be performed in real time and users may inspect and analyze the rendered volumetric image data interactively.

In the flow process 300, in step 308, image frames are formed by extracting 2D image maps from the volumetric image data. Specifically, two kinds of frames (i.e., critical frames) are formed. The first kind of critical frame may be a radically different frame which may be radically different from frames before and after it. The difference may be based on noise, an important feature, etc. The other kind of critical frame may be a representative frame. The process for extracting each of the two kinds of critical frames is depicted in FIGS. 4 and 5.

Figure 4:
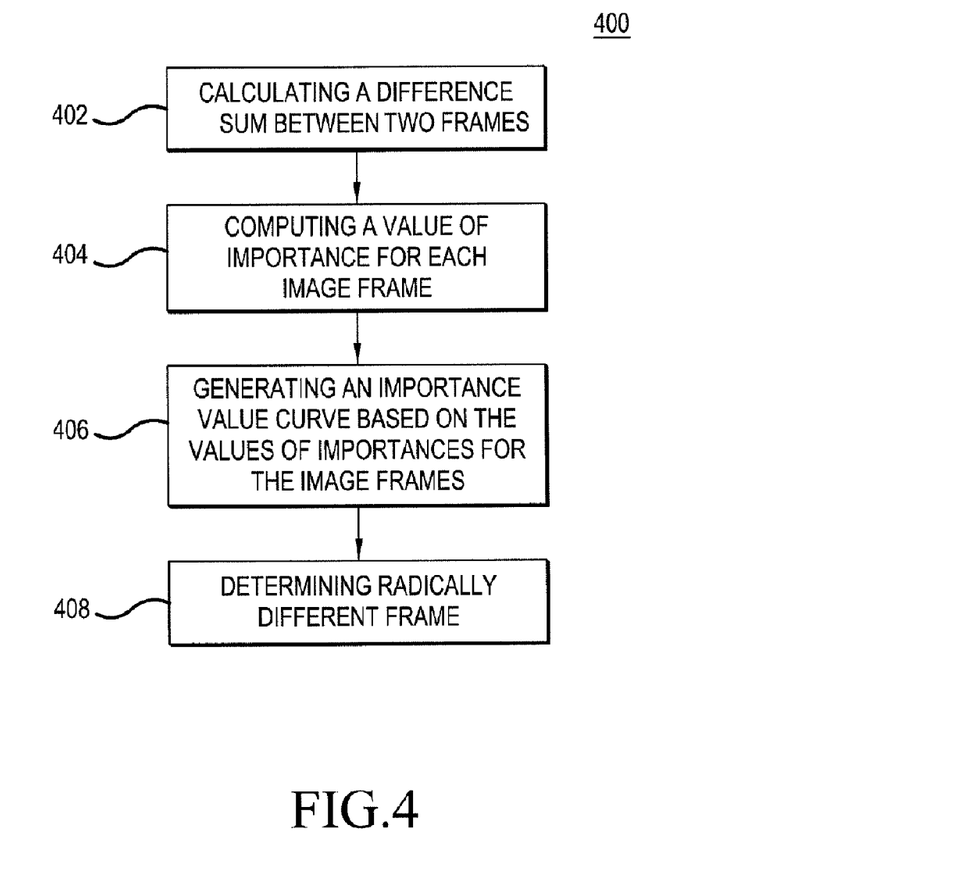
FIG. 4 is a flow diagram illustrating an example method of extracting 2D image maps to form image frames according to some embodiments of the present disclosure.

FIG. 4 depicts a flow process 400 for extracting a radically different frame. In step 402 a difference sum between two frames may be calculated by the sum of the square of difference between every two corresponding pixels of the two frames. In step 404, a value of importance of the frame at time t may be calculated as a Gaussian weighted sum of both the frame differences with the frame before and the frame after the frame under inspection. In step 406, an importance value curve is generated based on the values of importance for the frames calculated in step 404. In step 408, the frames with values of importance greater than a predetermined threshold are extracted as radically different frames. The predetermined threshold may be set by a user.

Figure 5:
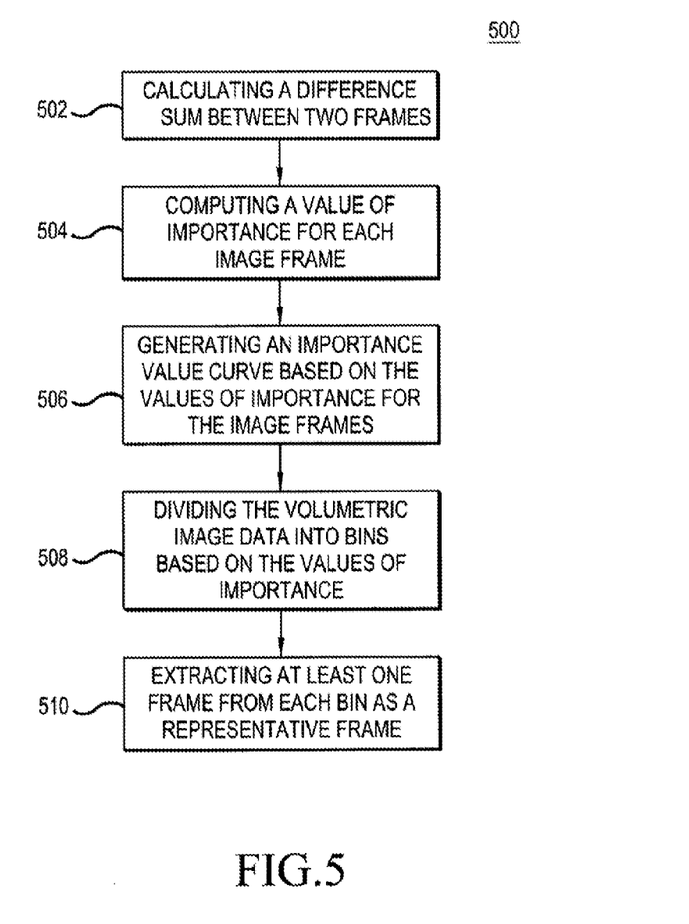
FIG. 5 is a flow diagram illustrating an example method of extracting 2D image maps to form image frames according to some embodiments of the present disclosure.

FIG. 5 depicts a flow process 500 for extracting a representative frame. In step 502 a difference sum between two frames may be calculated by the sum of the square of difference between every two corresponding pixels of the two frames. In step 504, a value of importance of the frame at time t may be calculated as a Gaussian weighted sum of both the frame differences with the frame before and the frame after the frame under inspection. In step 506, based on the values of importance for the frames calculated in step 504, an importance value curve is generated. In step 508, the volumetric image data may be divided into bins by dividing the whole data sequence over time with equal values of the integration of the importance value curve. The number of bins to be divided may be input by a user. In step 510, representative frames are extracted as the second kind of critical frames from each of the bins. The number of representative frames extracted for each bin may be input by a user. If more than one representative frame is extracted, each bin may be subdivided and a representative frame is then extracted from each subdivided bin. As such, the representative frames are extracted based on the integration of the importance values of the bins and each representative frame represents certain amount of importance.

Figure 6A:
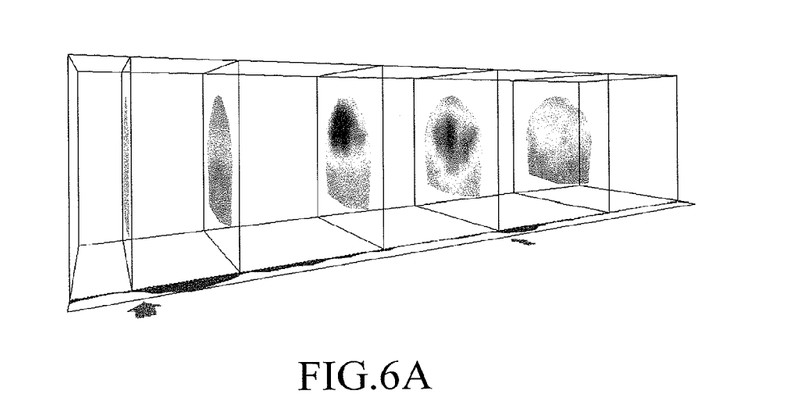
FIG. 6A depicts an example illustration of an image data of a frame gallery showing representative frames of an ERP volumetric image data.
Figure 6B:
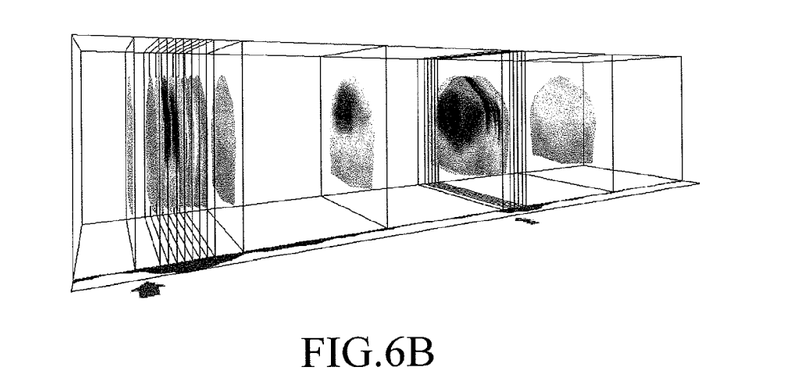
FIG. 6B depicts an example illustration of a frame gallery showing a combination of two kinds of critical frames.

In step 310 of the flow process 300, a frame gallery may be created from the two kinds of critical frames determined. In another embodiment, the process flow may proceed to step 312 to produce an image data based on the frame gallery obtained in step 310. FIG. 6(a) illustrates an example of frame gallery showing representative frames of an ERP volumetric image data. FIG. 6(b) illustrates an example of frame gallery showing a combination of both kinds of critical frames.

Figure 7A:
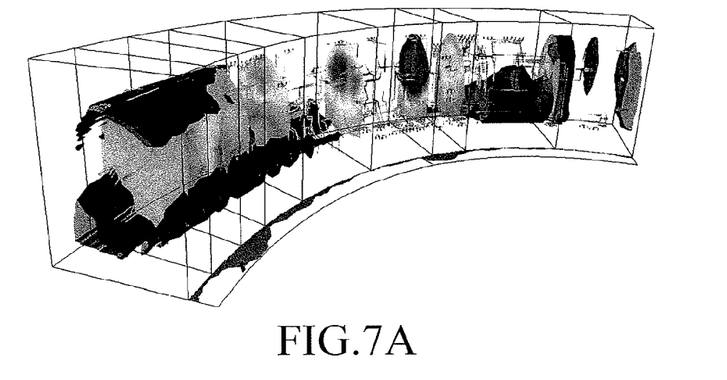
FIG. 7A depicts an example illustration of a composite image data of a volumetric image data with a frame gallery according to some embodiments of the present disclosure.
Figure 7B:
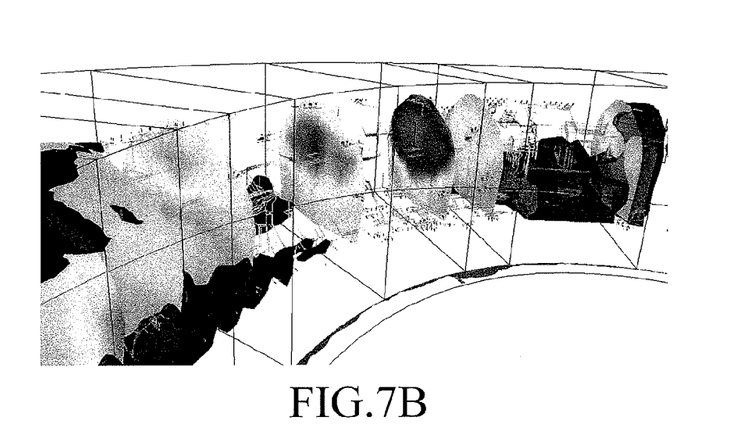
FIG. 7B depicts an example illustration of a zoom-in process being applied to the frame gallery of FIG. 7A
Figure 7C:
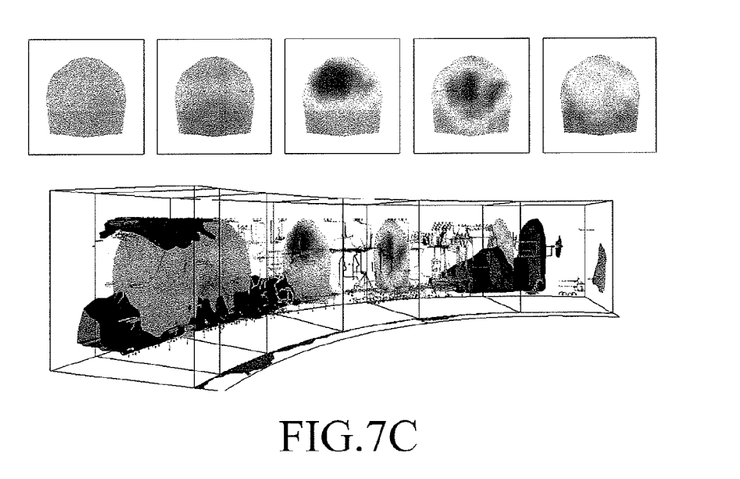
FIG. 7C depicts an example illustration of how the frame gallery may be rendered surrounding the volumetric image data.

In another embodiment, the process flow may proceed to step 316 to produce a composite image from the volumetric image data and the frame gallery. Specifically, the composite image may be produced in such a way that when the composite image may be rendered, the frame gallery may be rendered within the volumetric image data as shown as an example in FIG. 7(a). FIG. 7(b) shows a zoom-in process being applied to the frame gallery of FIG. 7(a). In addition, the frame gallery may be rendered surrounding the volumetric image data as shown as an example in FIG. 7(c). Moreover, the value of importance curve may be rendered along the bottom of the frame gallery. Thus, a user may explore the whole ERP time sequence data by comparing extracted frames. The method also allows users to dynamically change the sampling rate of focus or context region of the composite image rendered by an input device. By default, all frames are in the same size. The user may perform a zoom-in or zoom-out process on a frame or a part of the composite image rendered via an input device. Also, as shown in FIG. 7(a), (b) and (c), the whole ERP volume may be deformed in 3D and form a horseshoe shape to the occlusion between frames.

Example of Flow Process Implementation—Critical Point Graph

Figure 8:
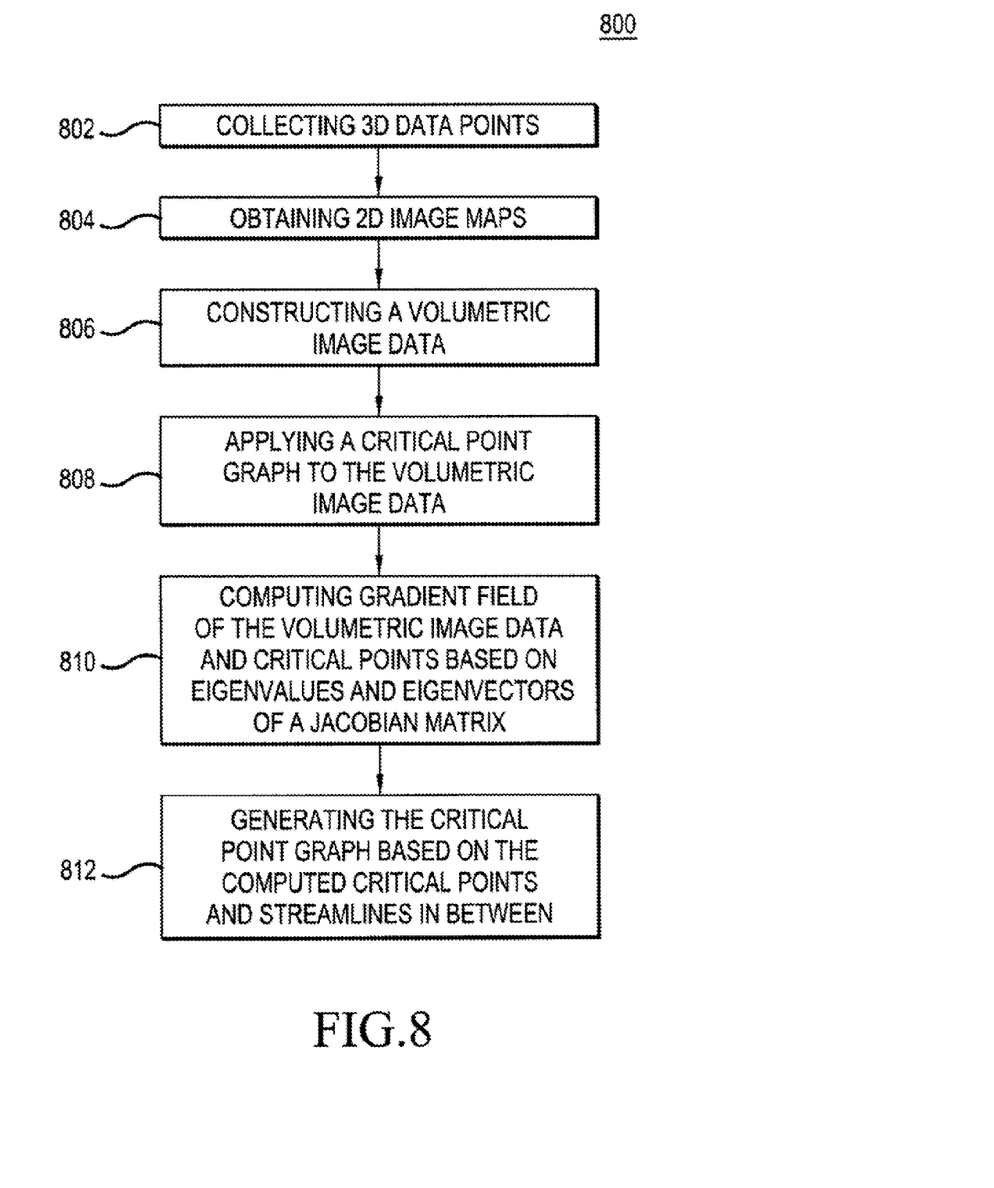
FIG. 8 is an example flow diagram illustrating a volumetric image data processing method according to some embodiments of the present disclosure.

FIG. 8 is a flow diagram depicting a volumetric image data process in accordance with another embodiment. Referring to the process flow 800, in step 802, data sets of 3D data points are collected to obtain 2D image maps in step 804. In step 802, the 3D data points may be collected from measurements carried out with measuring points spanning in 3D space. 3D data sets are generated from a spherical surface such as the event-related potential (ERP) data, ground measurement data, atmosphere temperature data and the like. For the purpose of discussion, ERP data sets generated over time will be used as a specific example. However, it should be understood that the methods, computer program and apparatus described herein may be applied to other data sets from the spherical surface. ERP data may be considered as a four-dimensional data set consisting of three spatial dimensions and time. ERP data is a group of potentials measured at different sensors over scalp of a person.

In step 804, the position of the measurement points of an ERP data of a specific time may be mapped to a 2D plane through projecting the original points in 3D space to a 2D plane by using a surface parameterization method. The surface parameterization method capable of minimizing distortion or minimizing computing effort may be chosen advantageously. A rectangle on the 2D plane may be defined as one may just cover all the projected points. Other shapes capable of covering all the projected points may be employed as well. The rectangle has certain resolution, which may be defined by acquiring an input from, for example, a user, to form a 2D image map. The image map may be a black-white one. A typical resolution could be N×N or M×N, e.g. 512×512, 512×256 and 256×256 as some examples. Each of the projected points has a position, i.e. coordinate, on the 2D image map. Data values of pixels not plotted in the 2D image map may be interpolated based on the neighboring pixels with the values assigned. One option could be a process where all plotted points are triangulated by using Delaunay Triangulation first, then interpolation may be carried out at the 2D image map by using Barycentric interpolation. The whole process may be carried out by using OpenGL APIs provided at chip level so as to save processing time. The ERP potentials may be plotted as intensity/gray scale at different points on the 2D image map, where all potential values experience a scaling process so as to fall into a gray scale range from 0% to 100%.

Steps 802 and 804 are performed on the ERP data taken from different time. In step 806, a volumetric image data is constructed from the 2D image maps generated in step 804. With each ERP volume slice, i.e., each image generated, an ERP volume may be constructed by stacking all data slices together along the time dimension. The ERP volume data includes the information of the ERP data of the whole time range. Because of the high temporal resolution of the ERP technique, ERP data sets usually contain thousands of sampling time points. Truncation on the data set and evenly sampling data at the time coordinate may be performed to reduce the size of the data set. 3D Gaussian filtering may also be performed on the data volume to reduce the noise.

In step 808, a critical point graph (CPG) is applied to the volumetric image data. In step 810, the gradient field of the original data volume is computed, then critical points are computed based the eigenvalues and eigenvectors of the Jacobian matrix. In step 812, the critical point graph (CPG) is generated based on the computed critical points and streamlines in between.

The streamlines are tangent to the vector field direction defined in each given point. In the case of ERP, the structure of the computed CPG may be an indication of the underlying brain activity.

Figure 9:
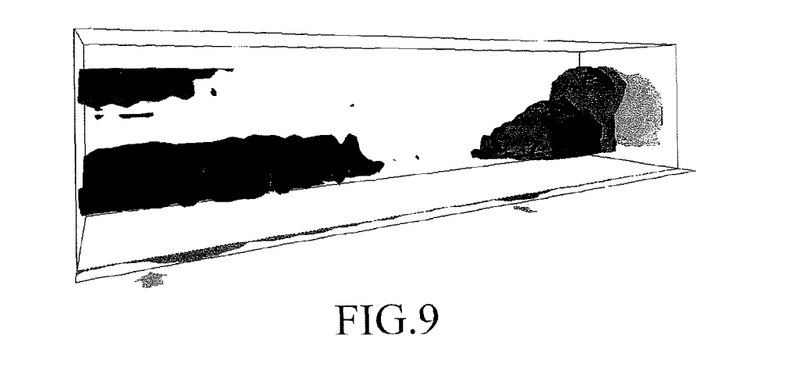
FIG. 9 depicts an example illustration of a volumetric image data with iso-surface process application according to some embodiments of the present disclosure.

The ERP paradigm may further involve at least two experimental conditions and an ERP volume may be generated for each of the experimental conditions. A difference volume may be generated by calculating the difference between the ERP volumes of the different experimental conditions. Furthermore, in constructing the volumetric image data, an iso-surface extraction process may be applied to generate an iso-surface at certain value. An example of a volumetric image data with iso-surface process application is illustrated in FIG. 9. Iso-surface extraction could be performed on both volumes generated from a single ERP data set and difference volumes. The classic marching cubes algorithm may be implemented.

Figure 10:
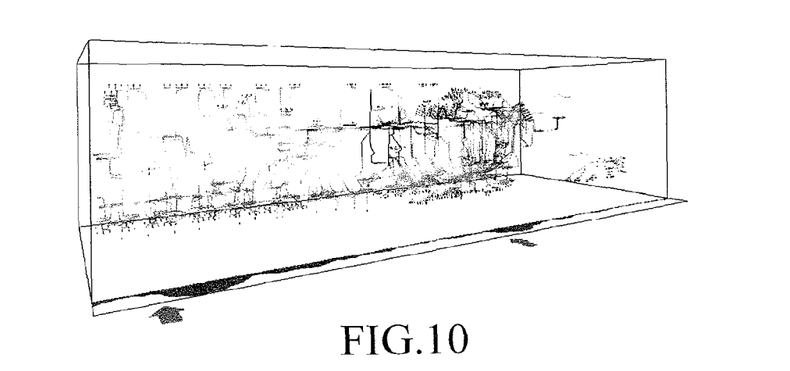
FIG. 10 depicts an example illustration of a volumetric image data with critical point graph application according to some embodiments of the present disclosure.
Figure 11:
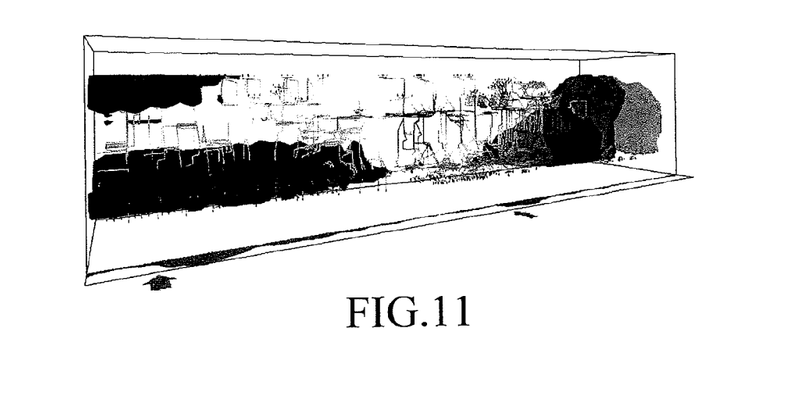
FIG. 11 depicts an example illustration of a volumetric image data with both iso-surface process and critical point graph application according to some embodiments of the present disclosure.

An example of a volumetric image data with CPG is illustrated in FIG. 10. Additionally, FIG. 11 illustrates an example of a volumetric image data with both iso-surface process and CPG application.

Additional Implementations

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one and one or more" to introduce claim recitations. However, the use of such phrases should not be construed to imply that the introduction of a claim recitation by the indefinite articles "a" or "an" limits any particular claim containing such introduced claim recitation to disclosures containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed:

1. A method for processing volumetric image data comprising:

obtaining a plurality of 2-dimensional image maps from 3-dimensional data points;

extracting at least one of the plurality of 2-dimensional image maps to form a plurality of image frames; and creating a frame gallery from the plurality of image frames including a radically different frame that is radically different from preceding and following frames based on a value of importance, wherein the value of importance includes a Gaussian weighted sum of the preceding frame and the radically different frame and the following frame and the radically different frame.

2. The method of claim 1, wherein the 3-dimensional data points are generated from a spherical surface.

3. The method of claim 1, wherein the 3-dimensional data points are generated from event-related potential (ERP) data.

4. The method of claim 1, wherein the radically different frame is radically different from the preceding and following frames based on the value of importance being greater than a predetermined threshold.

5. An apparatus for processing volumetric image data comprising:

an obtaining unit that obtains a plurality of 2-dimensional image maps from 3-dimensional data points;

an extracting unit that extracts at least one of the plurality of 2-dimensional image maps to form a plurality of image frames; and a creating unit that creates a frame gallery from the plurality of image frames including a radically different frame that is radically different from preceding and following frames based on a value of importance,
wherein the value of importance includes a Gaussian weighted sum of the preceding frame and the radically different frame and the following frame and the radically different frame.

6. The apparatus of claim 5, wherein the 3-dimensional data points are generated from a spherical surface.

7. The apparatus of claim 5, wherein the 3-dimensional data points are generated from event-related potential (ERP) data.

8. The apparatus of claim 5, wherein the radically different frame is radically different from the preceding and following frames based on the value of importance being greater than a predetermined threshold.

9. A method for processing volumetric image data, comprising:
    obtaining a plurality of 2-dimensional image maps from 3-dimensional data points;
    constructing a volumetric image data based on the plurality of 2-dimensional image maps and temporal data associated with each of the plurality of 2-dimensional image maps;
    applying a critical point graph to the volumetric image data; and
    creating a frame gallery from a plurality of image frames including at least one of a radically different frame or a representative frame,
    wherein a radically different frame is determined by:
        calculating a difference sum between two image frames by the sum of the square of difference between all corresponding pixels of the two image frames; and
        computing a value of importance for each image frame based on the calculated difference sum, the radically different frame being determined based on the computed value of importance for each image frame; and
    wherein a representative frame is determined by:
        calculating a difference sum between two image frames by the sum of the square of difference between all corresponding pixels of the two image frames;
        computing a value of importance for each image frame based on the calculated difference sum; and
        dividing the volumetric image data into bins based on the computed value of importance for each image frame, one frame from each of the bins being extracted as the representative frame.

10. The method of claim 9, wherein the applying a critical point graph comprises:
    computing a gradient field of the volumetric image data and critical points based on eigenvalues and eigenvectors of a Jacobian matrix; and
    generating the critical point graph based on the computed critical points and streamlines in between.

11. The method of claim 9, wherein the 3-dimensional data points are generated from a spherical surface.

12. The method of claim 9, wherein the 3-dimensional data points are generated from event-related potential (ERP) data.

13. A method for processing volumetric image data comprising:
    obtaining a plurality of 2-dimensional image maps from 3-dimensional data points;
    extracting at least one of the plurality of 2-dimensional image maps to form a plurality of image frames; and
    creating a frame gallery from the plurality of image frames including a representative frame that represents a certain amount of importance relative to preceding and following frames,
    wherein the value of importance includes a Gaussian weighted sum of the preceding frame and the representative frame and the following frame and the representative frame.

14. The method of claim 13, wherein the 3-dimensional data points are generated from a spherical surface.

15. The method of claim 13, wherein the 3-dimensional data points are generated from event-related potential (ERP) data.

16. An apparatus for processing volumetric image data comprising:
    an obtaining unit that obtains a plurality of 2-dimensional image maps from 3-dimensional data points;
    an extracting unit that extracts at least one of the plurality of 2-dimensional image maps to form a plurality of image frames; and
    a creating unit that creates a frame gallery from the plurality of image frames including a representative frame that represents a certain amount of importance relative to preceding and following frames,
    wherein the amount of importance includes a Gaussian weighted sum of the preceding frame and the representative frame and the following frame and the representative frame.

17. The apparatus of claim 16, wherein the 3-dimensional data points are generated from a spherical surface.

18. The apparatus of claim 16, wherein the 3-dimensional data points are generated from event-related potential (ERP) data.

19. A method for processing volumetric image data, comprising:
    obtaining a plurality of 2-dimensional image maps from 3-dimensional data points;
    constructing a volumetric image data based on the plurality of 2-dimensional image maps and temporal data associated with each of the plurality of 2-dimensional image maps;
    applying a critical point graph to the volumetric image data; and
    creating a frame gallery from a plurality of image frames including a representative frame that represents a certain amount of importance relative to preceding and following frames,
    wherein the amount of importance includes a Gaussian weighted sum of the preceding frame and the representative frame and the following frame and the representative frame.

20. The method of claim 19, wherein the 3-dimensional data points are generated from a spherical surface.

21. The method of claim 19, wherein the 3-dimensional data points are generated from event-related potential (ERP) data.

* * * * *

UNITED STATES PATENT AND TRADEMARK OFFICE
CERTIFICATE OF CORRECTION

PATENT NO. : 8,934,708 B2
APPLICATION NO. : 13/837956
DATED : January 13, 2015
INVENTOR(S) : Yuan

Page 1 of 1

It is certified that error appears in the above-identified patent and that said Letters Patent is hereby corrected as shown below:

On the title page, item 56, under "OTHER PUBLICATIONS", in Column 1, Line 1, delete "et al," and insert -- et al., --, therefor.

In the drawings

In Fig. 2, Sheet 2 of 9, delete "uP/uC/DSP" and insert -- μP/μC/DSP --, therefor.

In Fig. 2, Sheet 2 of 9, delete " " and insert --  --, therefor.

In the specification

In Column 1, Below Title, insert -- CROSS-REFERENCE TO RELATED APPLICATIONS
This application is a continuation under 35 U.S.C. §120 of U.S. Application Serial No. 12/569,480, filed September 29, 2009, now Pat. No. 8,437,538. --.

In Column 2, Line 34, delete "DRAWING" and insert -- DRAWINGS --, therefor.

In Column 4, Line 3, delete "Network 100" and insert -- Network 102 --, therefor.

In Column 10, Line 52, delete "and or" and insert -- and/or --, therefor.

Signed and Sealed this
Second Day of February, 2016

Michelle K. Lee
*Director of the United States Patent and Trademark Office*